United States Patent [19]

Bernard et al.

[11] Patent Number: 6,063,967
[45] Date of Patent: May 16, 2000

[54] PREPARATION OF PICRIC ACID

[75] Inventors: Laurent Bernard, Venissieux; Pascal Metivier, Ste Foy les Lyon, both of France

[73] Assignee: Rhone-Poulenc Chimie, Courbevoie Cedex, France

[21] Appl. No.: 09/094,595

[22] Filed: Jun. 15, 1998

Related U.S. Application Data

[63] Continuation of application No. 08/524,988, Sep. 8, 1995, abandoned.

[30] Foreign Application Priority Data

Sep. 9, 1994 [FR] France .................................. 94 10781

[51] Int. Cl.$^7$ .................................................. C07C 205/00
[52] U.S. Cl. ................................................. 568/710
[58] Field of Search ............................................. 568/710

[56] References Cited

U.S. PATENT DOCUMENTS 1,349,802   8/1920   Badier et al. ........................... 568/710
1,393,714  10/1921   Stine et al. ............................ 568/710

FOREIGN PATENT DOCUMENTS 011005   7/1919   United Kingdom .

OTHER PUBLICATIONS

Organic Chemistry, 3$^{rd}$ Ed., Hendricksen et al., pp. 660–662, 1970.

Primary Examiner—Kathleen K. Fonda
Attorney, Agent, or Firm—Burns, Doane, Swecker & Mathis, L.L.P.

[57] ABSTRACT

Picric acid, namely, 2,4,6-trinitrophenol, is readily and effectively prepared by nitrating o-nitrophenol and/or p-nitrophenol into at least one dinitrophenol in a nitric acid medium of reaction, characteristically essentially consisting of nitric acid or immixture thereof with a strong co-acid, the at least one dinitrophenol remaining soluble in the medium of reaction, and therein completing nitration of the at least one dinitrophenol and precipitating picric acid therefrom.

15 Claims, No Drawings

PREPARATION OF PICRIC ACID

This application is a continuation of application Ser. No. 08/524,988, filed on Sep. 8, 1995, now abandoned.

BACKGROUND OF THE INVENTION

1. Technical Field of the Invention

The present invention relates to a novel process for the preparation of picric acid.

2. Description of the Prior Art

Picric acid, or 2,4,6-trinitrophenol, is a known compound having a wide variety of industrial applications and, more particularly, for the production of explosives, medicaments, colorants and other applications (Tadeusz Urbanski, *Chemistry and Technology of Explosives*, Pergamon Press, pp. 498 (1964)).

Two principal routes are described in the literature for the preparation of picric acid, namely, sulfonitration of phenol or nitration of a dinitrophenol which is prepared via the hydrolysis of chlorodinitrobenzene.

The first entails a two-step process, comprising a step for sulfonation of the phenol and then a step for nitration of the sulfonated phenol thus obtained.

However, such a process suffers from a number of disadvantages, i.e., the sulfonation operation is lengthy and provides a low level of productivity and the nitration sequence is then effected in a reaction medium which is already dilute, which results in a decrease in productivity.

The other technique for preparing picric acid also comprises a plurality of steps, namely, nitration of monochlorobenzene to provide chlorodinitrobenzene, followed by hydrolysis of the product thus obtained, and then nitration of the dinitrophenol by means of a mixture of nitric acid and oleum.

This latter process is also not satisfactory as it too is lengthy, complicated and promotes pollution by virtue of the formation of sodium chloride in the hydrolysis step. Dealing with the saline aqueous effluents thus formed presents a serious drawback.

SUMMARY OF THE INVENTION

Accordingly, a major object of the present invention is the provision of an improved process for the preparation of picric acid that avoids or conspicuously ameliorates the above disadvantages and drawbacks to date characterizing the state of this art.

Briefly, the present invention features the preparation of picric acid, comprising first nitrating o-nitrophenol and/or p-nitrophenol into dinitrophenol(s) in such manner that said intermediate compound or compounds formed remain soluble in the reaction medium, and then continuing the nitration of the dinitrophenol or dinitrophenols to produce the picric acid which thus precipitates from the medium of reaction.

DETAILED DESCRIPTION OF BEST MODE AND PREFERRED EMBODIMENTS OF THE INVENTION

More particularly according to the present invention, a dinitrophenol is an intermediate compound, i.e., 2,4-dinitrophenol when the initial substrate or starting material is p-nitrophenol and a mixture of isomers, namely, 2,4-dinitrophenol and 2,6-dinitrophenol, which are produced from o-nitrophenol.

Hence, it has now unexpectedly been determined that picric acid can be prepared from o-nitrophenol and/or p-nitrophenol, insofar as the intermediate compound does not precipitate in the medium of reaction, as, once precipitated, it is no longer possible to nitrate this compound.

Therefore, it is important to control the absence of precipitation of the 2,4-dinitrophenol or the mixture of 2,4- and 2,6-dinitrophenols.

Consistent herewith, the intermediate product or products thus formed must remain soluble in the medium of reaction, characteristically by control of the concentration of the starting substrate, which depends on the particular technique for conducting the subject process, whether same is discontinuous or continuous. It is obviously intended to tolerate a small amount of the intermediate products in precipitated form, preferably less than 3%, and, more preferably, less than 1%, but this minor amount may lessen the reaction yield.

A first embodiment of the invention entails introducing nitric acid or a nitrating mixture into the o-nitrophenol and/or the p-nitrophenol.

By the term "nitrating mixture" is intended the combination of nitric acid, as described below, with a strong co-acid.

The o-nitrophenol can be utilized in the solid state, in the molten state, or in solution in the co-acid. As regards the p-nitrophenol, it can be employed in solid state, in solution in the co-acid or mixed with water, in the form of an eutectic mixture.

In this embodiment, in particular, it is desirable to ensure that the concentration of the dinitrophenol or dinitrophenols in the reaction medium is such that it or they remain soluble under the conditions of the reaction.

Thus, at a given temperature, the concentration of dinitrophenol or dinitrophenols is maintained lower than the level of concentration at which precipitation of the dinitrophenol or dinitrophenols is initiated.

The amount of dinitrophenol(s) solubilized depends on the reaction temperature and the acidity of the medium.

It will be appreciated, for example, that the level or degree of solubility of 2,4-dinitrophenol at 65° C. in a 95% aqueous sulfuric acid solution is about 12%.

It should also be appreciated that controlling the level of concentration of intermediate product(s) is also applicable to the other techniques for introducing the reactants. However, the concentration being a factor which limits productivity, other controls which are preferred may be employed.

In another embodiment of the invention, the p-nitrophenol and/or o-nitrophenol are progressively introduced into the reaction medium comprising nitric acid or the nitrating mixture, or, in parallel, the p-nitrophenol and/or o-nitrophenol and nitric acid, or the nitrating mixture, are simultaneously introduced into an initial bottoms material which comprises water or the co-acid.

By the term "progressive introduction" is intended addition continuously, or in a plurality of fractions.

The o-nitrophenol can be employed in solid state, in the molten state, or in solution in the co-acid. With respect to the p-nitrophenol, it can be employed in solid state, in solution in the co-acid, or mixed with water, in the form of an eutectic mixture.

In such event, the rate of introduction of the o-nitrophenol and/or p-nitrophenol must be selected at a value less than the rate of nitration of the dinitrophenol or dinitrophenols.

The rate of nitration depends on many parameters, in particular temperature, and the concentration of nitric acid, co-acid and dinitrophenol(s).

In that event it is possible to provide a concentration in respect of starting substrate which is higher, while maintaining the level of solubility of the dinitrophenol or dinitrophenols in the medium of reaction.

It is possible to select a proper rate of nitration by conducting routine determinations by analyzing the precipitate obtained which is to be picric acid.

The starting materials according to the process of the invention comprise o-nitrophenol or p-nitrophenol, or mixtures thereof.

When the starting substrate is introduced into the solution of co-acid, its concentration advantageously ranges from 20% to 80% by weight, preferably from 25% to 35% by weight.

In accordance with the process of the invention, the nitration operation can be carried out via two embodiments.

A first embodiment entails using only nitric acid.

This variant entails use of an aqueous solution of nitric acid of any concentration which can range from 30% to 100%. However, a concentration ranging from 68% to 100% is preferred.

In such event, the nitric acid is used in great excess. The amount of nitric acid thus constitutes from 4 to 10 times the weight of o-nitrophenol and/or p-nitrophenol.

Another embodiment of the invention entails combining nitric acid with another strong acid, hereinafter the "co-acid."

By the term strong acid is intended an acid having a pKa in water of less than −0.1 and, preferably, less than −1.0.

The pKa is defined as the ionic dissociation constant of the acid/base pair when water is used as the solvent.

Among the acids which satisfy that definition, it is preferable to use those which are stable in relation to nitric oxidation.

Particularly exemplary thereof are halogenated or nonhalogenated oxyacids such as sulfuric acid, pyrosulfuric acid, phosphoric acid, polyphosphoric acids, perchloric acid, halogenosulfonic acids such as fluorosulfonic acid, chlorosulfonic acid or trifluoromethanesulfonic acid, methanesulfonic acid, ethanesulfonic acid, ethane disulfonic acid, benzenesulfonic acid, benzenedisulfonic acids, toluenesulfonic acids, naphthalenesulfonic acids and naphthalenedisulfonic acids.

Among such acids, sulfuric acid or phosphoric acid are more particularly preferred.

A more preferred co-acid is sulfuric acid and a concentrated solution of sulfuric acid is preferably employed. The concentration in respect of sulfuric acid is preferably selected to be greater than 90% by weight and even more preferably greater than 98% by weight.

It is possible to replace the sulfuric acid with oleum reagents. These comprise $SO_3$ in varying amounts, preferably from 20% to 50% by weight.

The amount of nitric acid employed, expressed by the ratio of the number of moles of nitric acid and the number of moles of o-nitrophenol and/or p-nitrophenol advantageously ranges from about 2 to about 3 and more preferably from 2 to 2.2.

The amount of co-acid may vary over wide limits. It typically constitutes from 1 to 10 times the weight of o-nitrophenol and/or p-nitrophenol.

The process of the invention is advantageously carried out at a temperature of from 40° to 100° C., preferably from 40° C. to 70° C.

The process of the invention is generally carried out at atmospheric pressure, but it may also be carried out under slightly reduced pressure of, for example, from 500 and 760 mm of mercury.

It is not required to establish an atmosphere of inert gases.

From a practical standpoint, the process of the invention is easy to conduct as it does not require any particular apparatus.

In actual practice, the process of the invention is advantageously carried out as follows:

The different constituents of the reaction mixture are charged into the selected apparatus.

A variety of techniques, indicated above, are summarized in the following terms:

(a) the introduction of nitric acid or the nitrating mixture into o-nitrophenol and/or p-nitrophenol;

(b) the introduction of o-nitrophenol and/or p-nitrophenol into nitric acid or the nitrating mixture;

(c) the introduction, in parallel, of o-nitrophenol and/or p-nitrophenol and nitric acid, or the nitrating mixture, into a bottoms material comprising water or the co-acid.

The latter alternative embodiment is the preferred, the bottoms material being constituted by a solution of co-acid, preferably an aqueous solution of concentrated sulfuric acid, more preferably having a concentration of greater than 90%.

The duration of the operation of adding the o-nitrophenol and/or p-nitrophenol may range, for example, from 30 minutes to 4 hours, preferably from 1 to 2 hours.

After the reactants have been added, the reaction mixture is maintained in the temperature range indicated above for a few minutes (from 15 to 30 minutes).

At the end of the reaction, picric acid precipitates in the medium of reaction.

It can be separated using conventional solid/liquid separation techniques, preferably by filtration.

The product obtained is washed once or twice, preferably twice, with water. Picric acid is thus recovered.

One advantage of the process of the invention is that the picric acid is produced without transformation through a molten phase, which permits avoiding certain risks in respect of explosion at the point of manufacture.

In order to further illustrate the present invention and the advantages thereof, the following specific examples are given, it being understood that same are intended only as illustrative and in nowise limitative.

In said examples, the yields specified correspond to the following definitions:

$$\text{Yield: } RR = \frac{\text{Number of moles of picric acid formed}}{\text{Number of moles of n-nitrophenol}} \%$$

(or p-nitrophenol) transformed $$\text{Yield: } RT = \frac{\text{Number of moles of picric acid formed}}{\text{Number of moles of o-nitrophenol}} \%$$

(or p-nitrophenol) transformed

The abbreviations used in the examples have the following definitions:

ONP=o-nitrophenol

PNP=p-nitrophenol

EXAMPLE 1

The following reagents were introduced into a shott tube equipped with an agitation device, a condenser, a bubble counter and two push-syringes and which was heated by a thermostatically controlled bath:

(i) 15 g of an aqueous 95% sulfuric acid solution, and (ii) 2.74 g (20 mmol) of o-nitrophenol.

This was followed by the addition, with agitation, of 9.58 g (namely, 60.8 mmol of nitric acid) of a sulfonitric mixture containing 57% of sulfuric acid, 40% of nitric acid and 3% of water.

The procedure was commenced by adding one-third of said mixture at 43° C. over a period of time of 24 minutes and then two-thirds at 65° C. over 45 minutes. Heating was then maintained at 65° C. for 15 minutes.

The reaction medium was cooled and then poured over a mixture of 300 ml of ice-water/sulfamic acid (1 g) and a sufficient amount of methanol to provide a total volume of 1,000 ml.

The unreacted reactants and the products obtained were determined by high-performance liquid chromatography.

The results obtained are reported in Table I:

TABLE I

| Example | Substrate | $HNO_3$/ONP molar ratio | Order of charging operations | | Temp (° C.) | Duration (min) | RR-RT picric acid |
|---|---|---|---|---|---|---|---|
| | | | Bottom | Pouring | | | |
| 1 | ONP | 3 | ONP | Sulfonitric mixture | 43<br>65 | 24<br>45 + 15 | 94% |

EXAMPLE 2

Employing a 50 ml three-necked flask fitted with an agitation device, a condenser, a bubble counter and a push-syringe and heated by a thermostatically controlled bath, introduced therein were 20 g of a sulfonitric mixture containing 57% of sulfuric acid, 39% of nitric acid and 4% of water (i.e., 124 mmol of nitric acid).

The mixture was heated with agitation to 67° C. and then 23.76 g (34.2 mmol) of o-nitrophenol in a 20% solution in 95% sulfuric acid was poured therein, over a time period of 42 minutes.

Heating was then maintained at 67° C. for 15 minutes.

The reaction medium was cooled and then poured over a mixture of 300 ml of ice-water/sulfamic acid (1 g) and a sufficient amount of methanol to provide a total volume of 1,000 ml.

The unreacted reactants and the products obtained were determined by high-performance liquid chromatography.

The results obtained are reported in Table II:

TABLE II

| Example | Substrate | $HNO_3$/ONP molar ratio | Order of charging operations | | Temp (° C.) | Duration (min) | RR-RT picric acid |
|---|---|---|---|---|---|---|---|
| | | | Bottom | Pouring | | | |
| 2 | ONP | 3.6 | Sulfo-nitric mixture | ONP | 67 | 42 + 15 | 84% |

EXAMPLE 3

18.3 g of an aqueous 95% sulfuric acid solution was introduced into a 100 ml three-necked flask fitted with an agitation device, a condenser, a bubble counter and two push-syringes and which was heated by a thermostatically controlled bath.

Heating with agitation was effected to a temperature of 67° C. and then, over a period of 60 minutes, 28.2 g (40.6 mmol) of o-nitrophenol in 20% solution in 95% sulfuric acid and 19.52 g of a sulfonitric mixture containing 57% of sulfuric acid, 39% of nitric acid and 4% of water (namely, 121 mmol of nitric acid) were simultaneously poured therein.

Hearing at 67° C. was then maintained, for 15 minutes.

The reaction mixture was cooled and then poured over a mixture of 300 ml of ice-water/sulfamic acid (1 g) and a sufficient amount of methanol to provide a total volume of 1,000 ml.

The unreacted reactants and the products obtained were determined by high-performance liquid chromatography.

The results obtained are reported in Table III:

TABLE III

| Example | Substrate | HNO₃/ONP molar ratio | Order of charging operations Bottom | Order of charging operations Pouring | Temp (° C.) | Duration (min) | RR-RT picric acid |
|---|---|---|---|---|---|---|---|
| 3 | ONP | 3 | 95% H₂SO₄ | Simultaneous ONP sulfo-nitric mixture | 67 | 60 + 15 | 95% |

EXAMPLE 4

18.3 g of an aqueous 95% sulfuric acid solution were introduced into a 100 ml three-necked flask fitted with an agitation device, a condenser, a bubble counter and two push-syringes and which was heated by a thermostatically controlled bath.

Heating with agitation to a temperature of 67° C. was effected and then 28.34 g (40.8 mmol) of o-nitrophenol in 20% solution in 95% sulfuric acid and 13.58 g of a sulfonitric mixture containing 57% of sulfuric acid, 39% of nitric acid and 4% of water (namely, 84 mmol of nitric acid) were simultaneously poured therein.

Heating at 67° C. was then maintained for 19 minutes.

The reaction medium was cooled and poured over a mixture of 300 ml of ice-water/sulfamic acid (1 g) and a sufficient amount of methanol to provide a total volume of 1,000 ml.

The unreacted reactants and the products obtained were determined by high-performance liquid chromatography.

The results obtained are reported in Table IV:

TABLE IV

| Example | Substrate | HNO₃/ONP molar ratio | Order of charging operations Bottom | Order of charging operations Pouring | Temp (° C.) | Duration (min) | RR-RT picric acid |
|---|---|---|---|---|---|---|---|
| 4 | ONP | 2 | 95% H₂SO₄ | Simultaneous ONP sulfo-nitric mixture | 67 | 56 + 19 | 88% |

EXAMPLE 5

18.3 g of an aqueous 95% sulfuric acid solution were introduced into a 100 ml three-necked flask fitted with an agitation device, a condenser, a bubble counter and two push-syringes and which was heated by a thermostatically controlled bath.

Heating with agitation to 67° C. was effected and then 28.2 g (40.6 mmol) of p-nitrophenol in 20% solution in 95% sulfuric acid and 19.52 g of a sulfonitric mixture containing 57% of sulfuric acid, 39% of nitric acid and 4% of water (namely, 121 mmol of nitric acid) were poured simultaneously therein.

Heating at 67° C. was then maintained for 15 minutes.

The reaction medium was cooled and then poured over a mixture of 300 ml of ice-water/sulfamic acid (1 g) and a sufficient amount of methanol to provide a total volume of 1,000 ml.

The unreacted reactants and the products obtained were determined by high-performance liquid chromatography.

The results obtained are reported in Table V:

TABLE V

| Example | Substrate | HNO₃/ONP molar ratio | Order of charging operations Bottom | Order of charging operations Pouring | Temp (° C.) | Duration (min) | RR-RT picric acid |
|---|---|---|---|---|---|---|---|
| 5 | PNP | 3 | 95% H₂SO₄ | Simultaneous PNP sulfo-nitric mixture | 67 | 60 + 15 | 98% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of picric acid, said process comprising the steps of:
   (a) nitrating o-nitrophenol and/or p-nitrophenol into at least one dinitrophenol in a nitric acid reaction medium in the absence of an organic solvent at conditions effective to avoid precipitation of said at least one dinitrophenol in said reaction medium; and
   (b) nitrating said at least one dinitrophenol into picric acid.

2. The process as defined by claim 1, said nitric acid medium of reaction comprising a strong co-acid.

3. The process as defined by claims 1 or 2, comprising introducing said nitric acid medium of reaction into said o-nitrophenol and/or p-nitrophenol.

4. The process as defined by claim 2, comprising progressively introducing said o-nitrophenol and/or p-nitrophenol into said nitric acid medium of reaction.

5. The process as defined by claims 1 or 2, comprising separately introducing said o-nitrophenol and/or p-nitrophenol and nitric acid or medium comprised thereof into a bottoms vehicle which comprises water or said strong co-acid.

6. The process as defined by claims 1 or 2, which comprises nitrating o-nitrophenol, said o-nitrophenol comprising solid or molten state thereof, or solution of same in said strong co-acid.

7. The process as defined by claims 1 or 2, which comprises nitrating p-nitrophenol, said p-nitrophenol comprising solid state thereof, or solution in said strong co-acid or in admixture with water.

8. The process as defined by claim 1, said nitric acid medium of reaction essentially consisting of nitric acid.

9. The process as defined by claim 2, said nitric acid medium of reaction comprising admixture of nitric acid and said strong co-acid.

10. The process as defined by claim 9, said strong co-acid comprising a halogenated or nonhalogenated oxyacid, halogenosulfonic acid, or hydrocarbyl sulfonic acid.

11. The process as defined by claim 10, said strong co-acid comprising sulfuric acid, phosphoric acid or an oleum.

12. The process as defined by claim 1, the amount of nitric acid constituting from 4 to 10 times the weight of said o-nitrophenol and/or p-nitrophenol.

13. The process as defined by claim 1, wherein the ratio between the number of moles of nitric acid to the number of moles of said o-nitrophenol and/or p-nitrophenol ranges from 2 to 3.

14. The process as defined by claim 2, wherein the amount of said strong co-acid ranges from 1 to 10 times the weight of said o-nitrophenol and/or p-nitrophenol.

15. The process as defined by claim 1, carried out at a temperature ranging from 40° to 100° C.

* * * * *